(12) United States Patent
Kiani (10) Patent No.: US 8,663,107 B2
(45) Date of Patent: *Mar. 4, 2014

(54) SEPSIS MONITOR

(75) Inventor: Massi E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/100,172

(22) Filed: May 3, 2011

(65) Prior Publication Data

US 2011/0208018 A1    Aug. 25, 2011

Related U.S. Application Data (63) Continuation of application No. 11/803,936, filed on May 15, 2007, now Pat. No. 7,941,199.

(60) Provisional application No. 60/800,629, filed on May 15, 2006.

(51) Int. Cl.
*A61B 5/00* (2006.01)

(52) U.S. Cl.
USPC ............................. 600/301; 600/323; 600/324

(58) Field of Classification Search
USPC ......... 600/300, 301, 324, 500, 508, 529, 323; 128/900
See application file for complete search history.

(56) References Cited

U.S. PATENT DOCUMENTS

| | | |
|---|---|---|
| 4,869,253 A | 9/1989 | Craig, Jr. et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |

(Continued)

OTHER PUBLICATIONS

Angus, D.C., MD, MPH, FCCM, et al., "Epidemiology of Severe Sepsis in the United States: Analysis of Incidence, Outcome, and Associated Cost of Care," *Critical Care Medicine*, vol. 29, No. 7, pp. 1303-1310.

(Continued)

*Primary Examiner* — Bill Thomson
*Assistant Examiner* — Bobby Soriano
(74) *Attorney, Agent, or Firm* — Knobbe Martens Olson & Bear LLP (57) ABSTRACT

Sensors are attached to a living being so as to generate corresponding sensor signals. A monitor is in communications with the sensors so as to derive physiological parameters responsive to the sensor signals. Predetermined limits are applied to the physiological parameters. At least one indicator responsive to the physiological parameters and the predetermined limits signal the onset of a sepsis condition in the living being.

11 Claims, 6 Drawing Sheets

(56) References Cited

U.S. PATENT DOCUMENTS

| | | |
|---|---|---|
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,733,464 B2 * | 5/2004 | Olbrich et al. ............ 600/538 |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |

(56) References Cited

U.S. PATENT DOCUMENTS

| | | |
|---|---|---|
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,081,095 B2 * | 7/2006 | Lynn et al. .................. 600/538 |
| 7,090,648 B2 * | 8/2006 | Sackner et al. .................. 601/1 |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,252,637 B2 | 8/2007 | Ebner et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,668,579 B2 * | 2/2010 | Lynn ............................. 600/323 |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 2002/0103454 A1 * | 8/2002 | Sackner et al. ................. 604/19 |
| 2003/0191373 A1 * | 10/2003 | Blike ............................. 600/300 |
| 2003/0208113 A1 * | 11/2003 | Mault et al. .................... 600/316 |
| 2003/0214409 A1 * | 11/2003 | Hickle ........................ 340/573.1 |
| 2004/0039295 A1 | 2/2004 | Olbrich et al. |
| 2004/0078219 A1 | 4/2004 | Kaylor et al. |
| 2004/0186410 A1 * | 9/2004 | Davidner et al. ............ 604/5.01 |
| 2004/0236229 A1 * | 11/2004 | Freeman et al. ............... 600/474 |
| 2005/0001728 A1 | 1/2005 | Appelt et al. |
| 2005/0038332 A1 * | 2/2005 | Saidara et al. ................. 600/347 |
| 2005/0054942 A1 * | 3/2005 | Melker et al. .................. 600/532 |
| 2005/0065556 A1 * | 3/2005 | Reghabi et al. ................... 607/5 |
| 2005/0101841 A9 * | 5/2005 | Kaylor et al. ................... 600/300 |
| 2005/0143632 A1 * | 6/2005 | Elaz et al. ...................... 600/301 |
| 2005/0148832 A1 | 7/2005 | Reghabi et al. |
| 2005/0277912 A1 * | 12/2005 | John ........................... 604/890.1 |
| 2005/0288571 A1 * | 12/2005 | Perkins et al. .................. 600/407 |
| 2006/0020179 A1 * | 1/2006 | Anderson et al. .............. 600/309 |
| 2006/0155176 A1 * | 7/2006 | Ebner et al. .................... 600/301 |
| 2006/0241358 A1 * | 10/2006 | Al-Ali et al. ................... 600/301 |
| 2006/0276695 A9 * | 12/2006 | Lynn et al. ..................... 600/300 |
| 2007/0024946 A1 * | 2/2007 | Panasyuk et al. ............... 359/253 |
| 2007/0032733 A1 * | 2/2007 | Burton .......................... 600/509 |
| 2007/0093701 A1 * | 4/2007 | Myers et al. ................... 600/323 |
| 2007/0100213 A1 * | 5/2007 | Dossas et al. .................. 600/300 |
| 2007/0129647 A1 * | 6/2007 | Lynn ............................. 600/538 |
| 2007/0191697 A1 * | 8/2007 | Lynn et al. ..................... 600/323 |
| 2007/0219434 A1 * | 9/2007 | Abreu ........................... 600/301 |
| 2007/0282212 A1 * | 12/2007 | Sierra et al. .................... 600/529 |
| 2008/0051764 A1 * | 2/2008 | Dent et al. .................. 604/890.1 |
| 2008/0221408 A1 * | 9/2008 | Hoarau et al. .................. 600/310 |
| 2008/0286763 A1 * | 11/2008 | Russwurm et al. ................ 435/6 |
| 2008/0306353 A1 * | 12/2008 | Douglas et al. ................ 600/301 |
| 2009/0069642 A1 * | 3/2009 | Gao et al. ...................... 600/300 |
| 2009/0299154 A1 * | 12/2009 | Segman ......................... 600/301 |

OTHER PUBLICATIONS

Dellinger, R.P., MD, et al., "Surviving Sepsis Campaign Guidelines for Management of Severe Sepsis and Septic Shock," *Critical Care Medicine*, vol. 32, No. 3, pp. 858-873.

Masimo, "SpCO™ Pulse CO-Oximetry™", pp. 1-4 (2005).

Ohashi, K., et al., "Elevated Methemoglobin in Patients with Sepsis," *ACTA Anaesthesiologica Scandinavica*, 42, pp. 713-716 (1998).

(56) References Cited

OTHER PUBLICATIONS www.ccmjournal.com/pt/re/ccm/fulltext.00003246-199806000-00019.htm;jsessionid=, "Septic Shock: An Analysis of Outcomes for Patients with Onset on Hospital Wards Versus Intensive Care Units," *Critical Care Medicine*, vol. 26(6), 9 pages (Jun. 1998), downloaded and printed from the World Wide Web on Feb. 1, 2006.

http://www.ispub.com/ostia/index.php?xmlFilePath=journals/ijpn/vol2n2/sepsis.xml, "Plasma Carbon Monoxide Levels in Pediatrics Sepsis Syndrome," The Internet Journal of Pediatrics and Neonatology, vol. 2, No. 2, 11 pages (2002), downloaded and printed from the World Wide Web on Oct. 14, 2005.

* cited by examiner

SEPSIS MONITOR

CROSS-REFERENCE TO RELATED APPLICATIONS

The present application claims priority benefit under 35 U.S.C. §120 to, and is a continuation of U.S. patent application Ser. No. 11/803,936, filed May 15, 2007 entitled "Sepsis Monitor," which claims priority benefit under 35 U.S.C. §119(e) from U.S. Provisional Application No. 60/800,629, filed May 15, 2006, entitled "Septic Shock Monitor." The present application also incorporates the foregoing disclosures herein by reference.

BACKGROUND OF THE INVENTION

Sepsis is a serious medical condition caused by the body's response to an infection. The source of the infection can be any of a number of places throughout the body. Bacterial infections are the most common cause of sepsis, but sepsis can also be caused by fungal, parasitic, or viral infections. Toxins produced by an untreated or inadequately treated infection circulate in the bloodstream causing damage, for example, to the brain, heart, lungs, kidneys and liver. Severe sepsis can result in septic shock, a medical emergency in which the organs and tissues of the body are not receiving an adequate flow of blood.

SUMMARY OF THE INVENTION

The signs and symptoms of sepsis may be subtle. The unacceptably low survival rate of severe sepsis indicates that current patient identification strategies may be lacking. For example, conventional patient monitors give insufficient advance warning of deteriorating patient health or the onset of potentially serious physiological conditions resulting from sepsis. Advantageously, a sepsis monitor noninvasively measures patient condition so as to provide caregivers with an advanced warning or prediction of the onset sepsis. A sepsis monitor may also be configured to provide automatic intervention or treatment of sepsis.

SIRS (systemic inflammatory response syndrome) refers to the systemic activation of the body's immune response, such as from sepsis. SIRS is manifested by, for example, the presence of more than one of a temperature greater than 38° C. or less than 36° C.; a heart rate greater than 90 beats/min.; and a respiration rate greater than 20 breaths/min. Thus, in an embodiment, a sepsis monitor is responsive to more than one of pulse rate, respiration rate and temperature.

Sepsis also results in large amounts of nitrous oxide (NO) released into the blood. It has been shown that NO functions, in part, as a killer molecule that is activated by immune cells. The overproduction of NO during sepsis induces excessive vascular relaxation and a profound hypotension that is also a characteristic feature of sepsis. NO interacts rapidly with hemoglobin to form methemoglobin (HbMet). Thus, HbMet can function as a marker for NO generation in patients with sepsis. Further, endogenously produced CO functions as a messenger molecule as part of a complex cascade of mediators resulting from sepsis. A portion of the endogenous CO is exhaled and a portion is present as carboxyhemoglobin (HbCO). Thus, in an embodiment, a sepsis monitor is responsive to one or more of HbCO, HbMet and blood pressure.

In an embodiment, sepsis monitoring is based upon one or more physiological parameters and associated parameter limits, trends, patterns and variability, alone or in combination. The physiological parameters may include: blood parameters derived from an optical sensor including one or more of oxygen saturation ($SpO_2$), pulse rate, HbCO and HbMet; respiration rate (RR) derived from an acoustic sensor or a capnography sensor, as examples; noninvasive blood pressure (NIBP) derived from a blood pressure sensor, such as an inflatable cuff and corresponding acoustic sensor, a continuous NIBP(CNIBP) measurement device or an intelligent cuff inflation (ICI) device, to name a few; and temperature manually measured or derived from a thermistor or other temperature transducer.

One aspect of a sepsis monitor is sensors attached to a living being so as to generate corresponding sensor signals. A monitor is in communications with the sensors so as to derive physiological parameters responsive to the sensor signals. Predetermined limits are applied to the physiological parameters. At least one indicator responsive to the physiological parameters and the predetermined limits signal the onset of a sepsis condition in the living being.

Another aspect of a sepsis monitor is identifying physiological parameters indicative of an onset of a sepsis condition in a living being. Sensor signals are generated that are responsive to the physiological parameters. The physiological parameters are computed from the sensor signals. Predetermined rules are applied to the physiological parameters so as to determine the onset of the sepsis condition. An indicator signals the potential existence and likely nonexistence of the sepsis condition.

DETAILED DESCRIPTION OF THE PREFERRED EMBODIMENT

Figure 1:
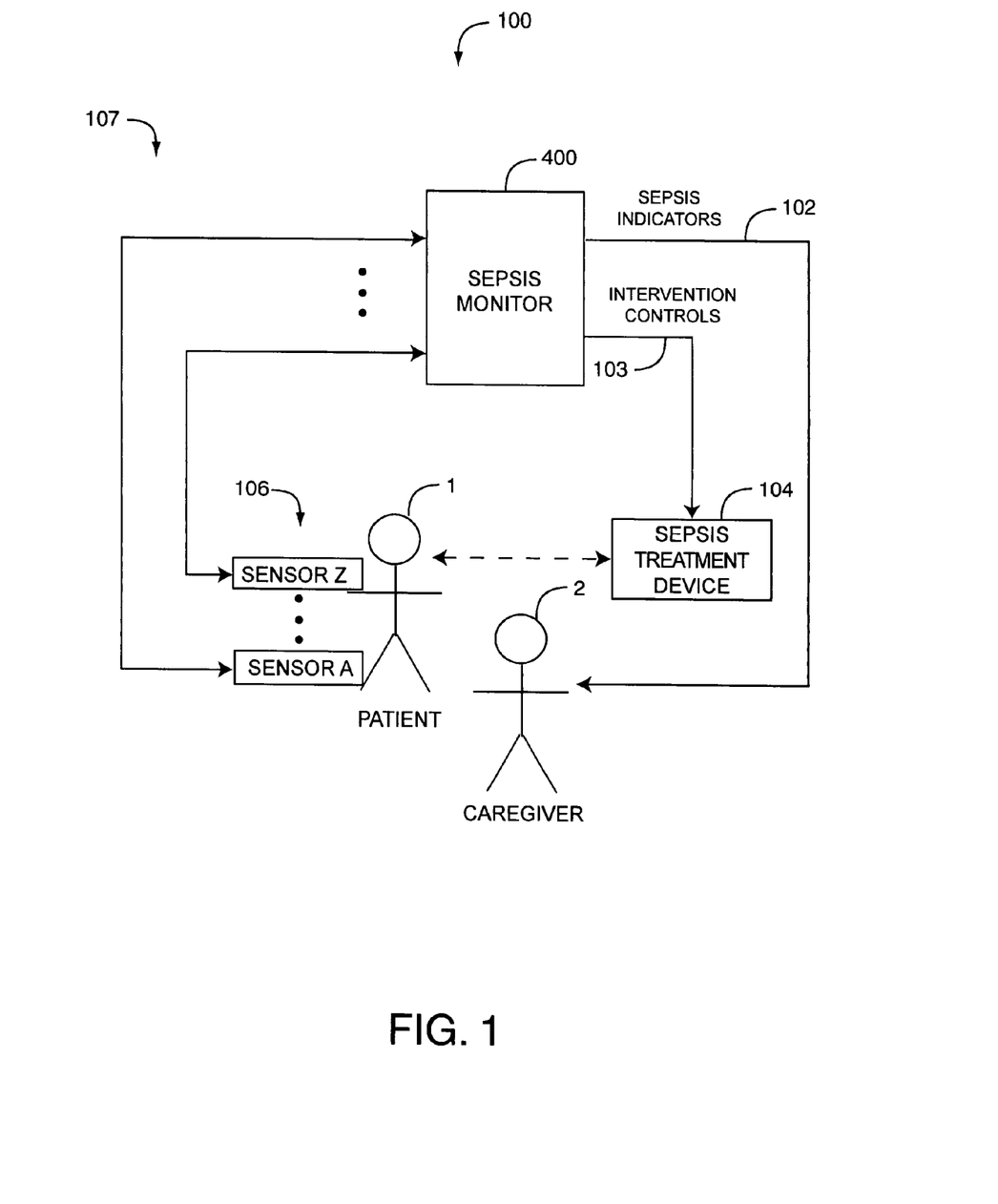
FIG. 1 is a general block diagram of a sepsis monitoring system.

FIG. 1 illustrates a sepsis monitoring system 100 having one or more sensors 106 generating sensor signals 107 in response to physiological states of a living being, such as a patient 1. A sepsis monitor 400 processes the sensor signals 107 and generates sepsis indicators 102 or intervention controls 103 or both, in response. In an open-loop configuration, one or more sepsis indicators 102 are observed by a caregiver 2, who administers treatment in response. Alternatively, or in addition, the caregiver 2 initiates, pauses, halts or adjusts the settings of a sepsis treatment device 104 in response to the sepsis indicators 102. In an embodiment, the sepsis indicators 102 signal one or more of a prediction of the onset of sepsis, a sepsis condition, a prediction of the onset of septic shock and a septic shock condition. In a closed-loop configuration, the sepsis treatment device 104 is responsive to one or more intervention controls 103 so as to affect the treatment of the patient 1, including, for example, initiating, pausing, halting or adjusting the dosage of administered drugs. In an embodiment, the intervention controls 103 are responsive to one or more of a prediction of the onset of sepsis, a sepsis condition, a prediction of the onset of septic shock and a septic shock condition.

As shown in FIG. 1, the sepsis treatment device 104 may be a drug infusion device, a medical gas inhalation device or a ventilation device to name a few. Drug infusion device and gas inhalation device control is described in U.S. patent application Ser. No. 11/654,904, filed Jan. 17, 2007, entitled Drug Administration Controller and incorporated by reference herein. Closed loop respirator control is described in U.S. patent application Ser. No. 11/585,678, filed Oct. 23, 2006, entitled Robust Ventilator Control and incorporated by reference herein.

As shown in FIG. 1, sensors 106 provide noninvasive measurements and include, for example, an optical sensor attached to a tissue site, such as a fingertip, for measuring one or more blood parameters. Noninvasive sensors 106 may also include acoustic sensors, blood pressure cuffs, ECG or EEG electrodes, $CO_2$ measuring capnography sensors and temperature sensors to name but a few. The sepsis monitor 400 is responsive to sensors signals 107 so as to generate parameter measurements, which may include $SpO_2$, pulse rate, perfusion index, perfusion variability index, HbCO, HbMet, total hemoglobin, fractional saturation, glucose, cyanide, respiration rate, blood pressure, $CO_2$, bilirubin, lung volume, cardiac output, temperature, consciousness and hydration measures, among other parameters. Such parameters may be measured intermittently or continuously. Although sensors 106 are described above with respect to noninvasive technologies, sensors 106 may be invasive or noninvasive. Invasive measurements may require a person to prepare a blood or tissue sample, which is then processed by an instrument or testing device, with the result read from the instrument or device and manually entered into the sepsis monitor 400.

The sepsis monitor 400 may be a single instrument incorporating various hardware, software, circuits and code for processing sensor signals, deriving physiological parameters and processing those parameters to generate the indicators and controls described above. Alternatively, the sepsis monitor 400 may integrate one or more standalone instruments or plug-ins, each of which process specific sensor signals and derive particular physiological parameters. These may include blood parameter monitors, respiration rate monitors, blood pressure monitors, ECG and EEG monitors and capnometers, as a few examples.

In an embodiment, sensors 106 include a multiple wavelength optical sensor, such as described in U.S. patent application Ser. No. 11/376,013, filed Mar. 1, 2006 and entitled Multiple Wavelength Sensor Emitters; and the sepsis monitor 400 incorporates a patient monitor, such as described in U.S. patent application Ser. No. 11/367,033, filed Mar. 1, 2006 and entitled Noninvasive Multi-Parameter Patient Monitor, both patent applications assigned to Masimo Laboratories, Irvine, Calif. and both incorporated by reference herein.

In an embodiment, sensors 106 and measurement devices 108 include multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters. The Rainbow™ sensors and RAD-57™ and Radical-7™ monitors are available from Masimo Corporation, Irvine, Calif. In an embodiment, sensors 106 include a pulse oximetry sensor, such as described in U.S. Pat. No. 5,782,757 entitled Low Noise Optical Probes and the sepsis monitor 400 incorporates a pulse oximeter, such as described in U.S. Pat. No. 5,632,272 entitled Signal Processing Apparatus, both assigned to Masimo Corporation, Irvine, Calif. and both incorporated by reference herein. In other embodiments, sensors 106 also include any of LNOP® adhesive or reusable sensors, SofTouch™ sensors, Hi-Fi Trauma™ or Blue™ sensor all available from Masimo Corporation, Irvine, Calif. Further, the sepsis monitor 400 may also include any of Radical®, SatShare™, Rad-9™, Rad-5™, Rad-5v™ or PPO+™ Masimo SET® pulse oximeters all available from Masimo Corporation, Irvine, Calif.

In another embodiment, the sepsis monitor 400 and the sepsis treatment device 104 are incorporated within a single unit. For example, the sepsis monitor 400 and treatment device 104 may be incorporated within a single housing, or the devices may be separately housed but physically and proximately connected.

Figure 2A:
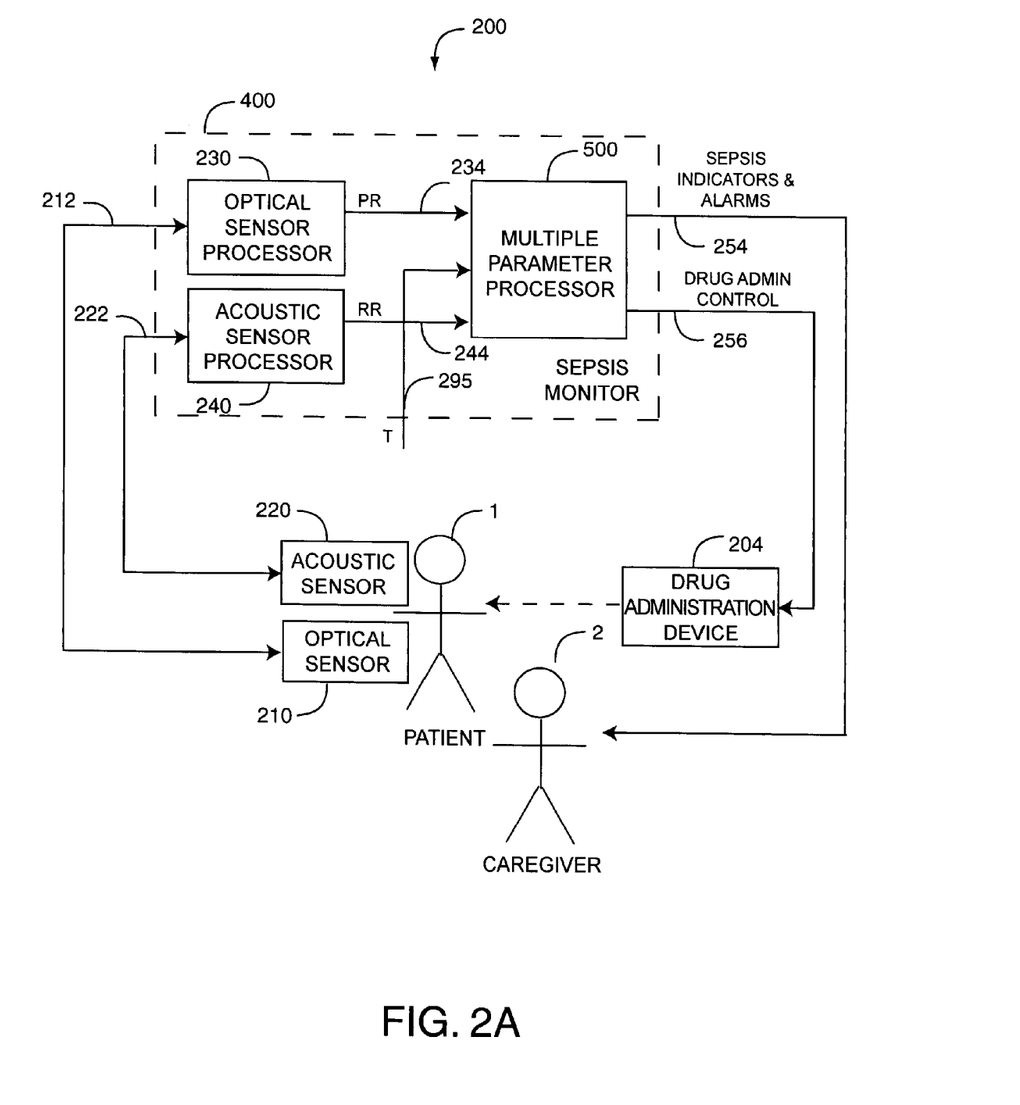
FIGS. 2A-B are detailed diagrams of sepsis monitoring system embodiments.
Figure 2B:
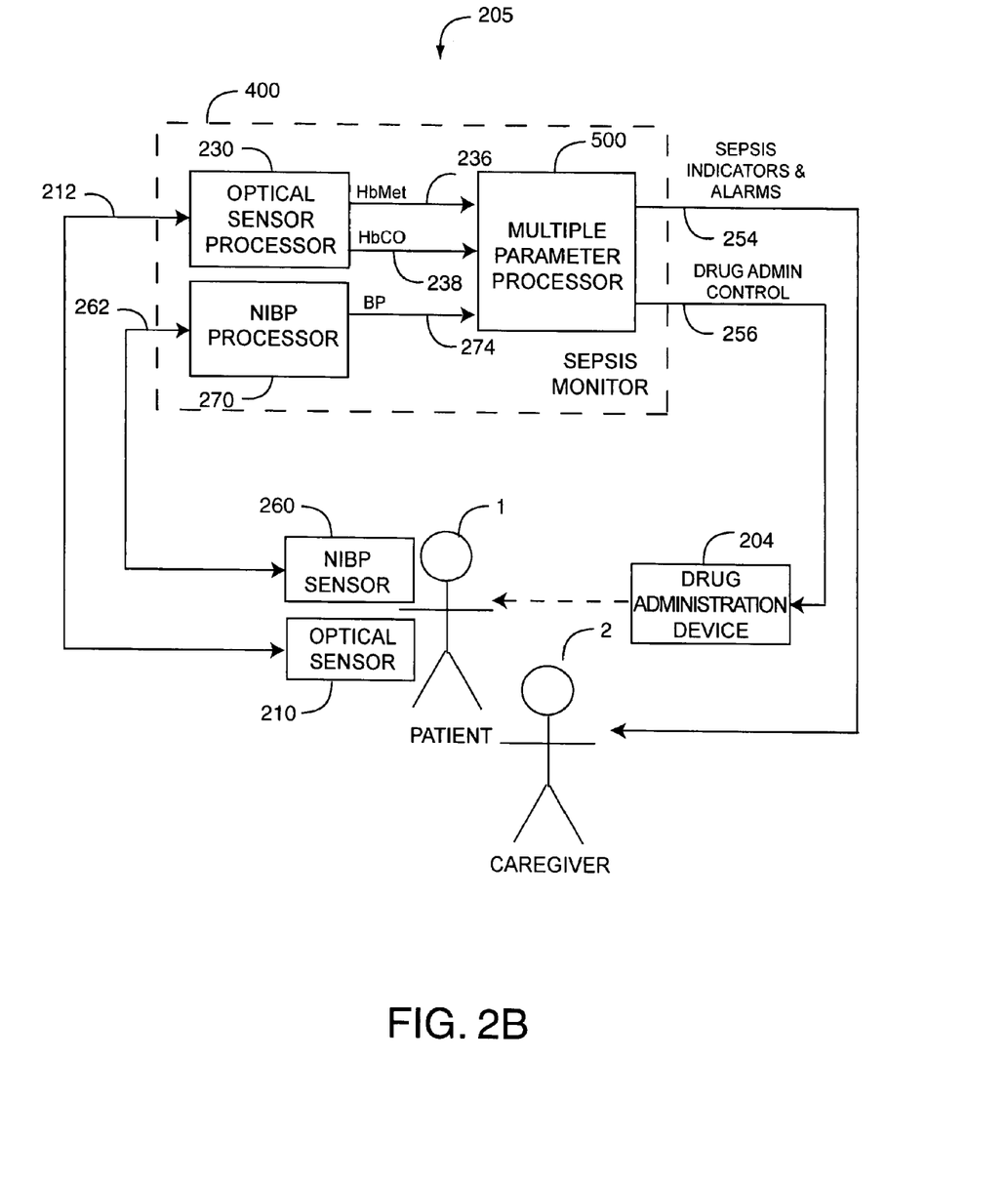

FIGS. 2A-B illustrate sepsis monitoring system embodiments 200, 205. As shown in FIG. 2A with respect to a system embodiment 200, a sepsis monitor 400 is in communications with an optical sensor 210 and an acoustic sensor 220 attached to a patient 1. An optical sensor processor 230 generates pulsatile-blood related parameters, such as pulse rate (PR) 234, in response to optical sensor signals 212. An acoustic sensor processor 240 generates body-sound related parameters 244, such as respiration rate (RR), in response to acoustic sensor signals 222. A temperature parameter 295 is generated via a temperature sensor or manually entered. A multiple parameter processor 500 processes the parameter measurements 234, 244, 295 alone or in combination and generates sepsis indicators and alarms 254 or drug administration controls 256, or both, in response. An acoustic sensor is described in U.S. Pat. No. 6,661,161 entitled Piezoelectric Biological Sound Monitor with Printed Circuit Board and a corresponding respirator rate monitor is described in International App. No. PCT/CA2005/000536 and PUb. No. WO 2005/096931, filed Apr. 8, 2005, both applications incorporated by reference herein.

As shown in FIG. 2B with respect to a system embodiment 205, a sepsis monitor 400 is in communications with an optical sensor 210 and a NIBP sensor 260 attached to a patient 1. An optical sensor processor 230 generates pulsatile-blood related parameters, such as such as HbCO 236 and HbMet 238 in response to optical sensor signals 212. An NIPB processor 270 generates blood pressure (BP) parameters, in response to NIBP sensor signals 262. A multiple parameter processor 500 processes the parameter measurements 236, 238, 274 alone or in combination and generates sepsis indicators and alarms 254 or drug administration controls 256, or both, in response. A continuous NIBP (CNIBP) sensor and processor are described in U.S. Pat. No. 5,590,649 entitled Apparatus and Method for Measuring an Induced Perturbation to Determine Blood Pressure and an intelligent cuff inflation (ICI) sensor and processor are described in U.S. Pat. No. 5,785,659 entitled Automatically Activated Blood Pressure Measurement Device, both patents incorporated by reference herein.

Advantageously, the multiple parameter processor 500 is responsive to a combination of multiple physiological parameters to indicate sepsis so that an alert can be provided based upon these parameters. Further, the multiple parameter processor 500 responds not only to parameter limits but also to parameter trend information, parameter patterns and parameter variability, so as to reflect a patient condition over time. In an embodiment, sepsis indicators 254 include alarms and wellness indicators that indicate stages of sepsis from none, to the onset of sepsis, to severe sepsis and septic shock. These outputs, for example, provide a warning of a potential onset of sepsis at an early stage and can trigger alarms as sepsis symptoms progress. Further, drug administration control 256 controls the administration of drugs or alters drug doses in response to patient condition. In an embodiment, the multiple parameter processor 500 compares parameter limits and rising or falling trends of the measurements 234, 244, 236, 238, 274, 295 alone or in combination, with corresponding predetermined thresholds and generates indicators and alarms 254 or drug administration controls 256 in response. The comparisons utilize a rule-based metric analysis, as described in detail in respect to FIGS. 4-5, below.

In one embodiment, the sepsis indicators 254 include a green indicator signaling a stable condition, a yellow indicator signaling a less stable condition or a potential sepsis onset and a red indicator signaling an unstable or severe sepsis condition. The indicators 254 may be, for example, various display LEDs emitting wavelengths of the appropriate colors. In an embodiment, a sepsis monitor 400 provides indicators 254 according to TABLES 1 and 2 below.

In an embodiment according to TABLE 1, below, if a patient's pulse rate (PR) and respiration rate (RR) are less than predetermined maximum limits and their body temperature is within a predetermined normal range, then the sepsis monitor 400 displays a green indicator. However, if more than one of pulse rate, respiration rate and body temperature are changing, where applicable changes in pulse rate and respiration rate are rate increases, then the sepsis monitor 400 displays a yellow indicator, signaling a potential onset of sepsis. If more than one of pulse rate, respiration rate and temperature become abnormal, including pulse rate and respiration rate above a predetermined limit and temperature outside of a predetermined range, then the sepsis monitor 400 displays a red indicator, signaling a potential sepsis condition.

TABLE 1

Rule-Based Monitor Outputs

| RULE | OUTPUT |
|---|---|
| If PR < heart rate limit; RR < breathing rate limit; & T in normal range. | Then illuminate green indicator. |
| If PR rising > heart rate trend limit; RR rising > breathing rate trend limit; & T rising or fallina. | Then illuminate yellow indicator |
| If PR > heart rate limit; RR > breathing rate limit; & T outside normal range. | Then illuminate red indicator; Trigger audible alarm. |

In an embodiment according to TABLE 2, below, if a patient's carboxyhemoglobin (HbCO), methemeglobin (HbMet) and blood pressure (BP) are normal, i.e. HbCO and HbMet less than predetermined maximum limits and BP greater than a predetermined minimum limit, then the sepsis monitor 400 displays a green indicator. However, if any of HbCO, HbMet and BP are changing, where applicable changes in HbCO and HbMet are increases and the applicable change in BP is a decrease, then the sepsis monitor 400 displays a yellow indicator, signaling a potential onset of sepsis. If any of HbCO, HbMet and BP change beyond predetermined limits, then the sepsis monitor 400 displays a red indicator, signaling a potential sepsis condition.

TABLE 2

Additional Rule-Based Monitor Outputs

| RULE | OUTPUT |
|---|---|
| If HbCO < CO limit; HbMet < Met limit; & BP > blood pressure limit. | Then illuminate green indicator. |
| If HbCO rising > CO trend limit; HbMet rising > Met trend limit or BP falling. | Then illuminate yellow indicator |
| If HbCO > HbCO limit threshold; HbMet > HbMet limit threshold; or BP < blood pressure limit. | Then trigger an alarm, such as An audible or a visual alert or both. |

In other embodiments, a sepsis monitor 400 utilizes predetermined limits and ranges on any or all of PR, RR, T, HbCO, HbMet and BP to indicate no sepsis, a potential onset of sepsis or a sepsis condition, with green, yellow and red indicators or with other visual and audible indicators, displays and alarms. Other indicators, alarms, controls and diagnostics in response to various combinations of parameters and thresholds can be substituted for, or added to, the rule-based outputs illustrated in TABLES 1 and 2.

Figure 5:
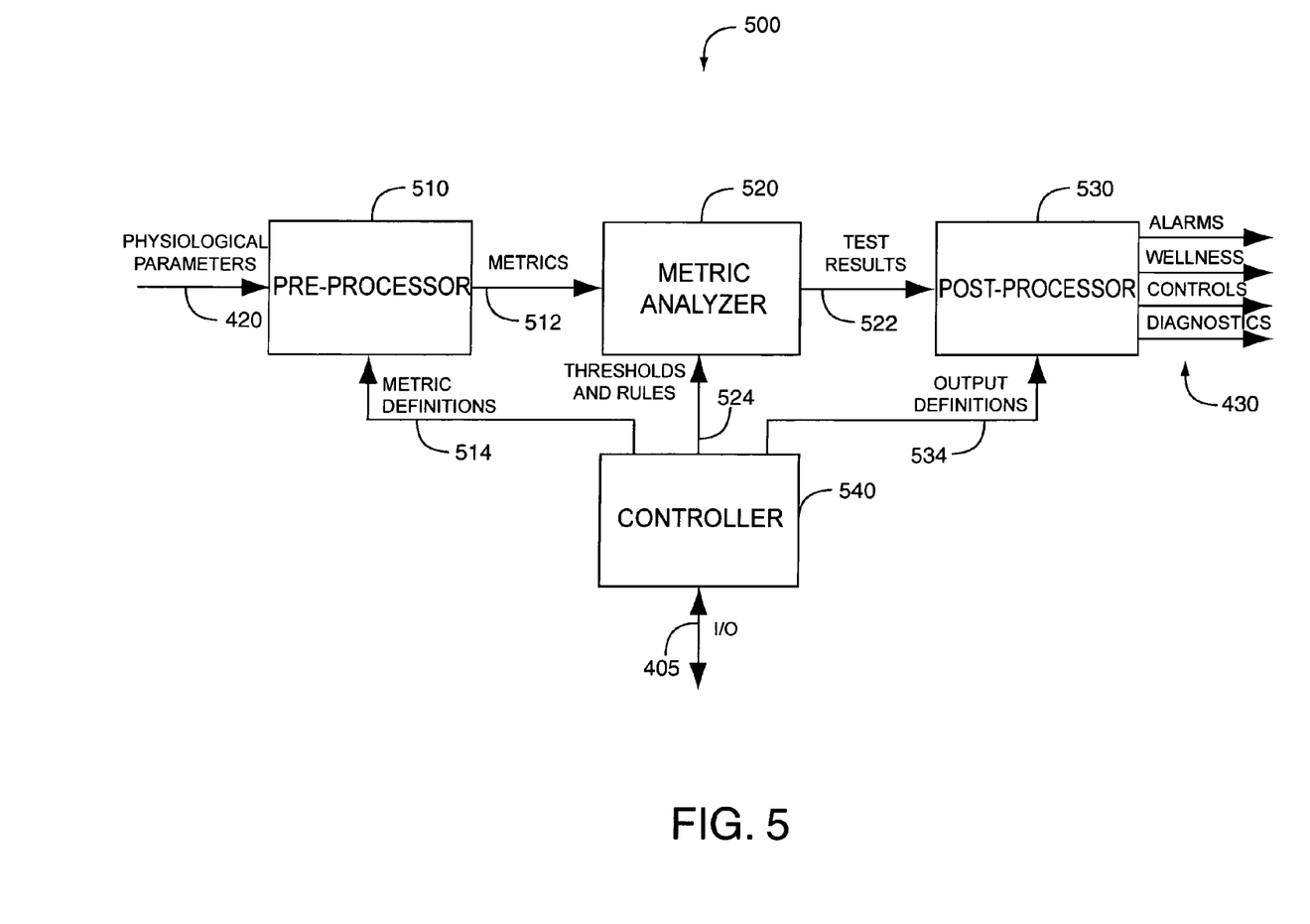
FIG. 5 is a detailed block diagram of a multiple parameter processor embodiment.

Other parameter measurements that may be input to the multiple parameter processor 500 include oxygen saturation ($SpO_2$) and perfusion index (PI) as derived from a pulse oximeter, EGG, EEG and $ETCO_2$, to name a few. All of these parameters may indicate real-time measurements and historical data such as measurement trends, patterns and variability. Signal quality measurements may also be input to the multiple parameter processor 500. Pulse oximetry signal quality and data confidence indicators are described in U.S. Pat. No. 6,684,090 entitled Pulse Oximetry Data Confidence Indicator, a pattern recognition alarm indicator is described in U.S. Pat. No. 6,822,564 entitled Parallel Measurement Alarm Processor, both patents assigned to Masimo Corporation, Irvine, Ga. and incorporated by reference herein.

Figure 3:
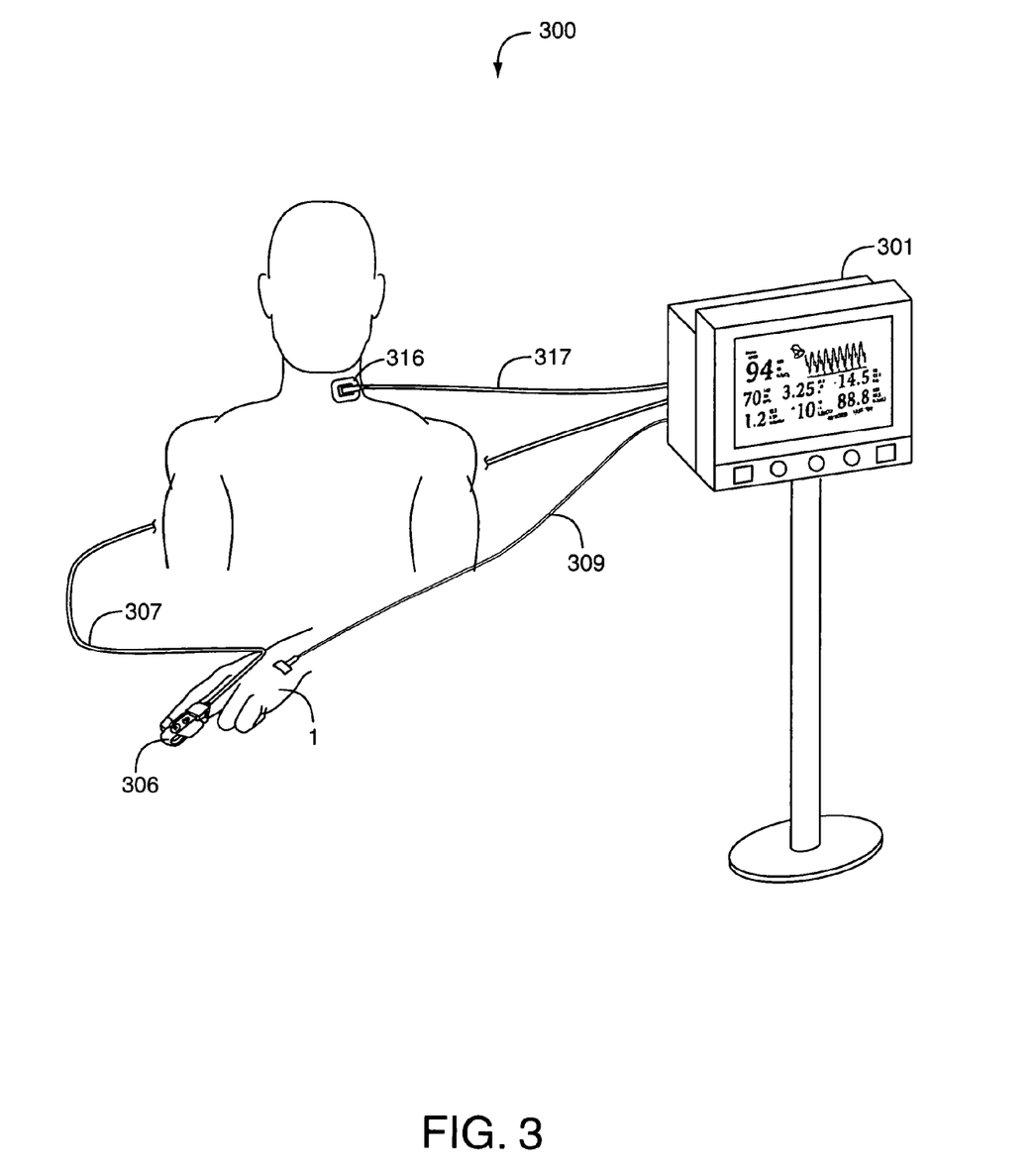
FIG. 3 is an illustration of a sepsis monitoring system embodiment.

FIG. 3 illustrates a sepsis monitoring system 300 combining a sepsis monitor 400 (FIG. 1) and a drug administration device 204 (FIGS. 2A-B) into a drug infusion monitor 301. The sepsis monitoring system 300 has an optical sensor 306 and a piezoelectric sensor 316 attached to a patient's body 1. The optical sensor 306 detects pulsatile blood components and the piezoelectric sensor 316 detects tracheal sounds. The corresponding optical and acoustic sensor signals are transmitted to the drug infusion monitor 301 via an optical-sensor cable 307 and an acoustic-sensor cable 317. The drug infusion monitor 301 generates blood parameter measurements such as PR, HbCO and HbMet and biological sound measurements such as respiration rate (RR) and processes the measurements to display sepsis indicators and administer corresponding treatments. In a particular embodiment, the drug infusion monitor 301 intravenously administers one or more drugs, such as recombinant activated protein C, to the patient 1 in doses and dose intervals so as to respond to varying stages of sepsis or the potential onset of sepsis and to transitions between less severe and more severe stages of sepsis.

Figure 4:
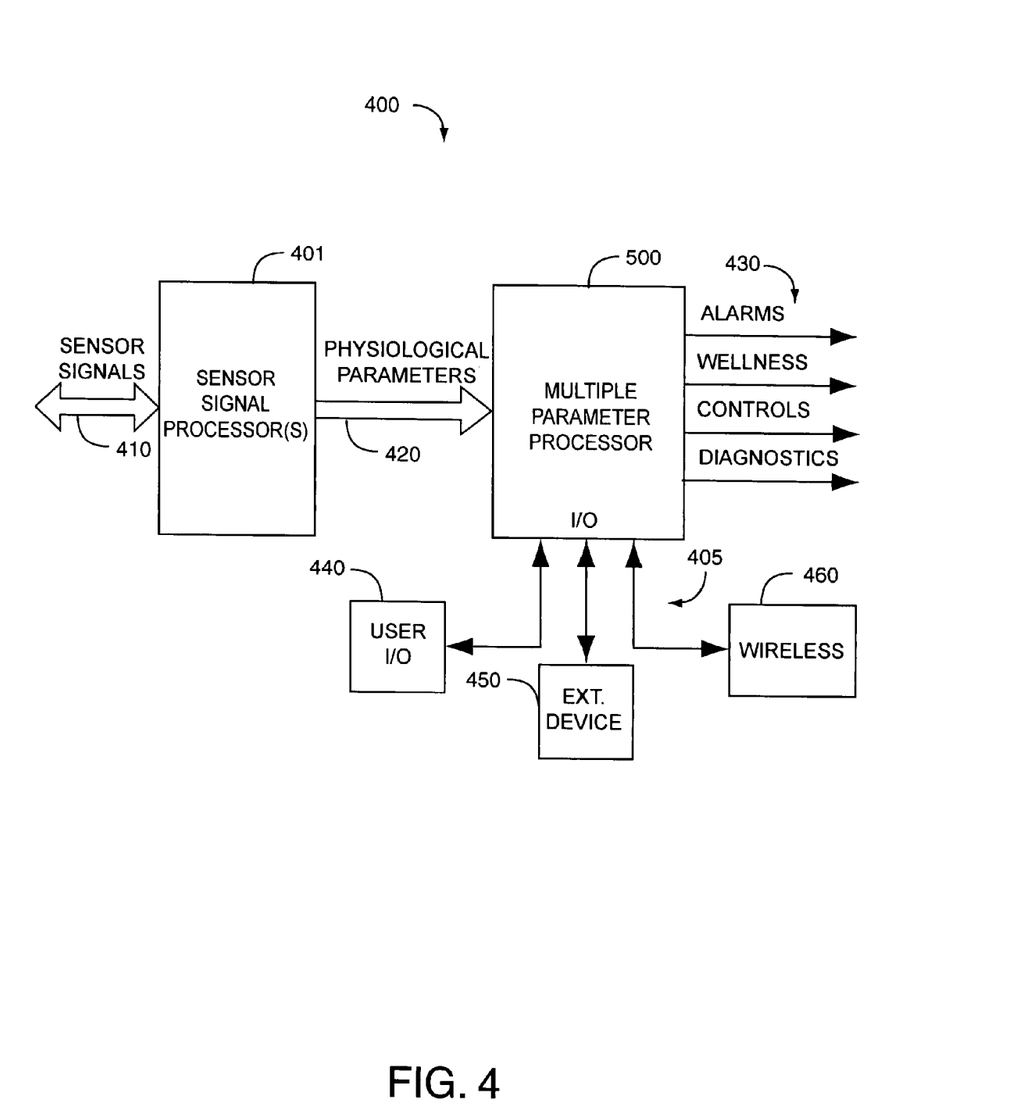
FIG. 4 is a general block diagram of a sepsis monitor incorporating a multiple parameter processor.

FIG. 4 illustrates a sepsis monitor embodiment 400 having sensor signal processor(s) 401, a multiple parameter processor 500, sensor signal inputs 410 to the signal processor(s) 401 and monitor outputs 430 from the parameter processor 500. Monitor outputs 430 may be sepsis alarms, wellness indicators, controls and sepsis diagnostics. Alarms may be used to alert medical personnel to a potential urgent or emergency medical condition in a patient under their care. Wellness indicators may be used to inform medical personnel as to patient condition stability or instability, such as a less urgent but potentially deteriorating medical state or condition. Diagnostics may be messages or other indicators used to assist medical personnel in diagnosing or treating a patient condition. Controls may be used to affect the operation of a medical treatment device, as described above, or other medical-related equipment.

In an embodiment, the multiple parameter processor 500 also has an input and output port (I/O) 405 that provides communications to the outside world. The I/O includes user I/O and external device communications to name a few. User I/O allows manual data entry and control. For example, a menu-driven operator display may be provided to allow entry of predetermined alarm thresholds. External device communications may include interfaces, networks or wireless communications to PCs, printers, chart recorders or displays to name a few.

FIG. 5 illustrates a sepsis monitor embodiment 500 having a pre-processor 510, a metric analyzer 520, a post-processor 530 and a controller 540. The pre-processor 510 has inputs 420 that may be real-time physiological parameter measurements, historical physiological parameter measurements, signal quality measures or any combination of the above. The pre-processor 510 generates metrics 512 that may include historical or real-time parameter trends, detected parameter patterns, parameter variability measures and signal quality indicators to name a few. As examples, trend metrics may indicate if a physiological parameter is increasing or decreasing at a certain rate over a certain time, pattern metrics may indicate if a parameter is cyclical within a particular frequency range or over a particular time period, variability metrics may indicate the extent of parameter stability.

As shown in FIG. 5, the metric analyzer 520 is configured to provide test results 522 to the post-processor based upon various rules applied to the metrics 512 in view of various thresholds 524. As an example, the metric analyzer 520 may output an alarm trigger 522 to the post-processor 530 when a parameter measurement 503 increases faster than a predetermined rate. This may be expressed, as an example, by a rule that states "if trend metric exceeds trend threshold then trigger alarm." TABLE 1 and TABLE 2, above, illustrate sepsis monitor rules applied to metrics including PR, RR, T, HbCO, HbMet and BP parameters and trends.

Also shown in FIG. 5, the post processor 530 inputs test results 522 and generates outputs 502 including alarms, wellness indictors, controls and diagnostics. Alarms may be, for example, audible or visual alerts warning of critical conditions that need immediate attention. Wellness indicators may be audible or visual cues, such as an intermittent, low-volume tone or a red/yellow/green light indicating a patient with a stable or unstable physiological condition, as examples. Controls may be electrical or electronic, wired or wireless or mechanical outputs, to name a few, capable of interfacing with and affecting another device. Diagnostics may indicate a particular patient condition, such as the potential onset of sepsis.

Further shown in FIG. 5, the controller 540 interfaces with I/O 509. In one embodiment, the I/O 509 provides predetermined thresholds, which the controller 540 transmits to the metric analyzer 520. The controller 540 may also define metrics 514 for the pre-processor 510 and define outputs 534 for the post-processor 530.

A sepsis monitor has been disclosed in detail in connection with various embodiments. These embodiments are disclosed by way of examples only and are not to limit the scope of the claims that follow. One of ordinary skill in art will appreciate many variations and modifications.

What is claimed is:

1. A patient monitoring method seeking to identify a sepsis condition in said patient, said method comprising:

noninvasively generating a plurality of sensor signals responsive to physiological parameters indicative of an onset of a sepsis condition in a said patient, at least one of said sensor signals responsive to the output of a noninvasive optical sensor;

electronically computing measurements for said physiological parameters from the sensor signals, said parameters including at least, pulse rate, temperature, and respiration;

said respiration parameter responsive to measurements taken by an acoustic sensor applied to the neck, and said pulse rate parameter responsive to measurements taken by a pulse oximeter applied to a digit;

applying a plurality of predetermined rules to the physiological parameters so as to determine the onset of the sepsis condition; and indicating to an observer the potential existence of the sepsis condition.

2. The sepsis monitoring method according to claim 1 wherein the acoustic sensor detects tracheal sounds of the living being.

3. The sepsis monitoring method according to claim 2 wherein the applying comprises determining if the temperature is outside a predetermined range.

4. The sepsis monitoring method according to claim 3 wherein the applying comprises determining if the pulse rate and the respiration rate are greater than a plurality of predetermined limits.

5. The sepsis monitoring method according to claim 4 wherein the indicating comprises activating a first colored light to indicate nonexistence of a sepsis condition and a second colored light to indicate a potential existence of a sepsis condition.

6. The sepsis monitoring method according to claim 1 further comprising sending a control signal to a drug administration device intravenously in communications with the living being in response to the applying step so as to provide treatment for the sepsis condition.

7. A method of electronically monitoring signals indicative of a patient condition to determine when to warn a caregiver that said patient condition is indicative of sepsis, the method comprising:

outputting a first signal from a noninvasive optical sensor applied to a digit indicative of an absorption of light by body tissue of said patient, said first signal also indicative of one or more physiological parameters of said patient including a pulse rate;

outputting a second signal from a noninvasive acoustic sensor applied to an area of skin around a patient's throat where said second signal is indicative of acoustically sensed tracheal sounds;

outputting a third signal from a thermal sensor wherein the signal is indicative of a temperature of the patient;

electronically processing with a processor said first signal to output measurement values for said one or more physiological parameters including at least the pulse rate, processing with said processor said second signal to output measurement values for respiration, and processing with said processor said third single to output measurement values for said temperature;

electronically applying with said processor a plurality of predetermined rules to said measurement values; and when said application of said rules indicates said patient condition is indicative that sepsis potentially exists, or that sepsis likely exists, outputting at least one of an audio or visual indication to said caregiver that sepsis potentially exists, or that sepsis likely exists respectively according to the indication from the application of the rules.

8. The method according to claim 7, wherein the audio or visual indication is a colored light.

9. The method according to claim 7, further comprising sending a control signal to a drug administration device intravenously in communications with said patient, said control signal responsive to said indication of said sepsis, said device providing treatment for said sepsis.

10. The method of claim 7, wherein the applying comprises determining if the pulse rate and the respiration rate are greater than a plurality of predetermined limits.

11. The method of claim 7, wherein the applying comprising determining if the temperature is outside a normal range.

* * * * *